US00PP23154P3

(12) United States Plant Patent
Brigham et al.

(10) Patent No.: US PP23,154 P3
(45) Date of Patent: Oct. 30, 2012

(54) ***HEMEROCALLIS* PLANT NAMED 'STRIPED FANTASTIC'**

(50) Latin Name: ***Hemerocallis* hybrid**
Varietal Denomination: Striped Fantastic

(76) Inventors: Steven Michael Brigham, Westport, CA (US); Donna Gunderson Brigham, Westport, CA (US)

( * ) Notice: Subject to any disclaimer, the term of this patent is extended or adjusted under 35 U.S.C. 154(b) by 302 days.

(21) Appl. No.: 12/798,880

(22) Filed: Apr. 12, 2010

(65) Prior Publication Data

US 2011/0252529 P1 Oct. 13, 2011

(51) Int. Cl.
*A01H 5/00* (2006.01)

(52) U.S. Cl. ..... Plt./312

(58) Field of Classification Search ..... Plt./312
See application file for complete search history.

(56) References Cited

U.S. PATENT DOCUMENTS

PP9,387 P * 11/1995 Iverson ..... Plt./312
PP14,221 P3 * 10/2003 Malan ..... Plt./312
PP22,181 P2 * 10/2011 Petit ..... Plt./312

* cited by examiner

*Primary Examiner* — Wendy C Haas
(74) *Attorney, Agent, or Firm* — Klarquist Sparkman, LLP

(57) ABSTRACT

A new and distinct cultivar of *Hemerocallis* plant characterized by striking variegated leaves combined with the beautiful and large flowers of *Hemerocallis* 'Kate Carpenter'.

1 Drawing Sheet

Botanical classification: *Hemerocallis* hybrid.
Variety denomination: 'Striped Fantastic'.

BACKGROUND OF THE INVENTION

The present invention relates to a new and distinct cultivar of an herbaceous perennial of the genus, *Hemerocallis*, and known by the cultivar name of 'Striped Fantastic'. The genus *Hemerocallis* is a member of the family Hemerocallidaceae. It is natural mutation of *Hemerocallis* 'Kate Carpenter' (an unpatented plant) found as a branch mutation in a cultivated area (a garden) in in San Marcos, Calif. in the spring of 1999. *Hemerocallis* 'Kate Carpenter' was bred by R. W. Munson in 1980.

SUMMARY OF THE INVENTION

This new cultivar is characterized by:

1) Dark green leaves with broad, creamy white margins giving the plant a long season of interest.
2) Excellent vigor.

This new cultivar has been reproduced only by asexual propagation (division and tissue culture). Each of the progeny exhibits identical characteristics to the original plant. Asexual propagation by tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The drawing shows a two-year-old *Hemerocallis* 'Striped Fantastic' growing in the ground in full sun in the trial field in September in Canby, Oreg.

DETAILED PLANT DESCRIPTION

The following is a detailed description of the new cultivar based on observations of two-year-old specimens in September grown in the ground in full sun in the trial garden in Canby, Oreg. The color descriptions are all based on The Royal Horticultural Society Colour Chart, 3rd edition.

Plant:

*Type.*—Herbaceous perennial.
*Form.*—Arching.
*Hardiness.*—USDA Zones 5 to 9.
*Size.*—90 cm wide and 70 cm tall from the soil surface to the top of the foliage.
*Habit.*—Clumping.
*Roots.*—Thick fleshy white roots with fine laterals.

Leaf:

*Type.*—Simple, basal.
*Arrangement.*—Rosette, two ranked.
*Shape.*—Linear, tapered, folded at the base.
*Venation.*—Parallel.
*Margins.*—Entire, sometimes slightly undulate.
*Apex.*—Attenuate.
*Base.*—Clasping.
*Size.*—72 cm long and 3 cm wide.
*Surface texture.*—Glabrous.
*Leaf color.*—Topside deep green in the leaf center, Green 137A to 138B, with a broad creamy white margin (5 to 10 mm), Yellow 4A, which narrows toward the tip and breaks into several stripes; bottom side Green 138B with creamy white margins and stripes, Yellow 4A.

Inflorescence:

*Type.*—Upright terminally branched determinant panicle.
*Number of flowers.*—Up to 17 per panicle per inflorescence.

*Size of inflorescence*.—Grows to 13 cm tall and 17 cm wide.

*Scape*.—About 7 in number, grows to 39 cm tall and 8 mm wide, glaucous, with small leaf like bracts at the nodes (variable in size, ovate, to 2.5 cm long, both sides 137B with margins Yellow 4A), Yellow Green 147B with striping up the stem Yellow 4D.

*Pedicel*.—18 to 23 mm long and 4 mm wide, glabrous, Yellow Green 147B, at a 15 degree angle from the vertical.

Flower bud:

*Size*.—9.2 cm long and 3 cm wide at the widest point prior to opening.

*Description*.—Tubular.

*Surface texture*.—Smooth, glabrous.

*Color*.—Yellow Orange 20C with base and tip Yellow Green N144D.

Flower:

*Type*.—Perfect, actinomorphic.

*Shape*.—Funnelform flowers with fused perianth, perianth segments separate.

*Size*.—13 mm wide and 10 mm deep.

*Tepal description*.—Inner tepals 3, broadly ovate to elliptic, reflex slightly, 8.5 cm long and 5 cm wide, bottom half with margins entire, top half margins ruffled, glabrous on both sides, tip obtuse, base attenuate, topside Yellow Orange 16C on outside ⅓, darkening to Yellow Orange 16B to midrib, midrib 22D lightening to Yellow 11D, and Yellow Green N144A near base, bottom side Yellow Orange 16B on the sides and 22B in the middle; outer tepals 3, elliptic, reflexed, 8.5 cm long and 3.5 cm wide, margins mostly entire with some ruffling near the tip, glabrous on both sides, tip acute, base attenuate, topside Yellow Orange 22C with Yellow Green N144D near base, bottom side Yellow Orange 20C.

*Pistil description*.—10.5 mm long, ovary 28 mm long and 8 mm wide, Yellow Green 145A, style 7.5 cm long, stigma and style Yellow Orange 20C.

*Stamen description*.—6 in number, filaments 4 cm long, Yellow 11A, anthers 10 mm long, Yellow Green 148A prior to dehiscence, pollen Yellow Orange 16A.

*Fragrance*.—None.

*Lastingness*.—A flowers blooms for about 2 days on the plant.

*Bloom period*.—June in Canby, Oreg.

Fruit: Capsule, not seen.

Seed: Not seen.

Pest and disease tolerance: The new cultivar is typical to the genus. No known resistances to pests or diseases. No problems have been found in Canby, Oreg.

The description by the American *Hemerocallis* Society for *Hemerocallis* 'Kate Carpenter' is as follows:

"The 1996 winner of the Lenington All-American Award_ voted annually by the AHS Board of Directors for a daylily that performs well over a wide geographic area_is KATE CARPENTER (Munson, R. W. 1980).

KATE CARPENTER (Munson, R. W. 1980) is a stylish very round, flat and ruffled creamy melon with a cream throat.

Height: 28"; Flower Size: 6"; Flower Characteristics: tetraploid, diurnal, fragrant; Season of Bloom: early, midseason, reblooms; Foliage habit: evergreen.

Parents: [(WILBUR HARDING×KECIA)×PAGODA GODDESS].

Awards: Junior Citation 1980, Honorable Mention 1986, Award of Merit 1989. Most Popular in AHS Region 7—1988, 1992; Lenington All-American Award 1996."

Comparisons to Similar Varieties

Compared to its mother plant, *Hemerocallis* 'Kate Carpenter' (an unpatented plant), the only difference is the leaf variegation. *Hemorocallis* 'STRIPED FANTASTIC' is variegated with creamy white margins while *Hemerocallis* 'Kate Carpenter' is not.

Compared to *Hemerocallis* 'Malja' also known as 'Striped Zebra' (U.S. Plant Pat. No. 14,221), the new variety is larger in size, has a lighter yellow variegation, and has larger flowers of creamy shades rather than yellow orange.

We claim:

1. A new and distinct hybrid of *Hemerocallis* plant substantially as shown and described.

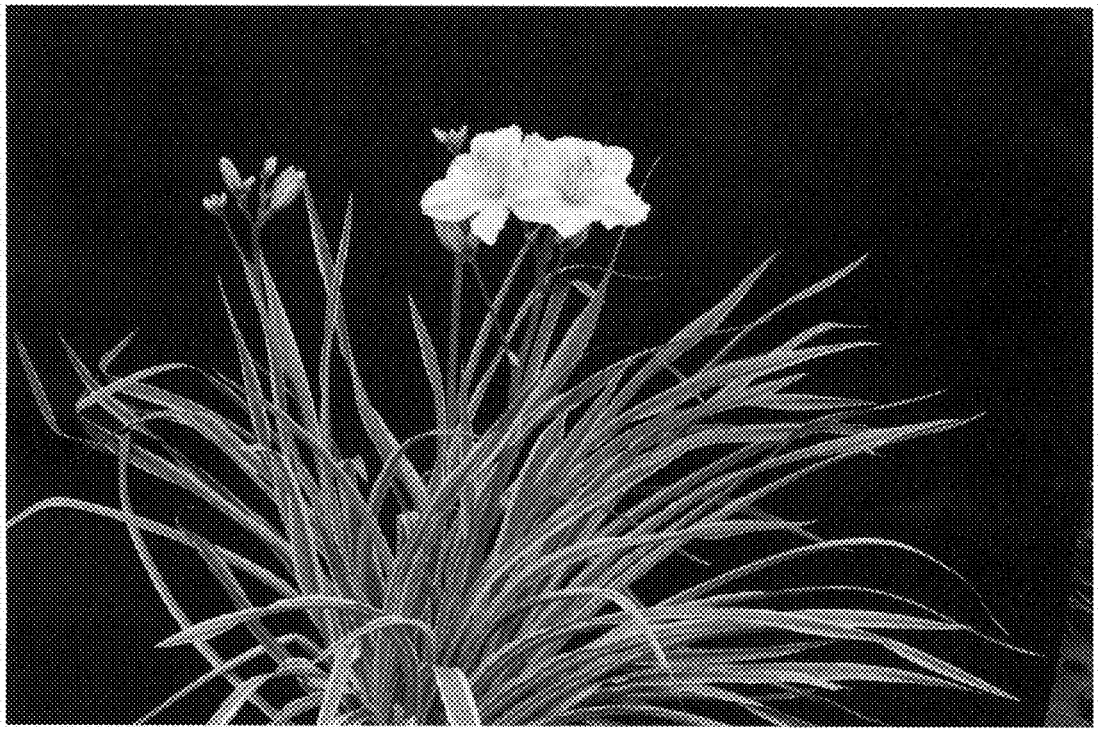

* * * * *